(12) United States Patent
Hendrickson

(10) Patent No.: US 9,057,014 B2
(45) Date of Patent: *Jun. 16, 2015

(54) HYDRAULIC FRACTURE COMPOSITION AND METHOD

(75) Inventor: Calder Hendrickson, Lubbock, TX (US)

(73) Assignee: AQUASMART ENTERPRISES, LLC

( * ) Notice: Subject to any disclaimer, the term of this patent is extended or adjusted under 35 U.S.C. 154(b) by 282 days.

This patent is subject to a terminal disclaimer.

(21) Appl. No.: 13/418,227

(22) Filed: Mar. 12, 2012

(65) Prior Publication Data

US 2012/0225800 A1    Sep. 6, 2012

Related U.S. Application Data

(63) Continuation-in-part of application No. 13/299,288, filed on Nov. 17, 2011, now Pat. No. 8,661,729, which is a continuation-in-part of application No. 12/789,177, filed on May 27, 2010, now Pat. No. 8,341,881, which is a continuation of application No. 12/324,608, filed on Nov. 26, 2008, now Pat. No. 7,726,070.

(60) Provisional application No. 61/012,912, filed on Dec. 11, 2007.

(51) Int. Cl.
*E21B 43/26* (2006.01)
*C09K 8/80* (2006.01)
*A01N 25/34* (2006.01)
*E21B 43/267* (2006.01)

(52) U.S. Cl.
CPC ............... *C09K 8/805* (2013.01); *E21B 43/267* (2013.01); *A01N 25/34* (2013.01)

(58) Field of Classification Search
CPC ............ C09K 8/805; C09K 8/80; C09K 8/62; C04B 2103/0049; C04B 20/1011; E21B 43/267; E21B 43/26; Y10S 507/924; Y10S 507/92

USPC ..................................................... 47/58.1 SC
See application file for complete search history.

(56) References Cited

U.S. PATENT DOCUMENTS

2,991,267 A    7/1961    Bean
3,442,803 A    5/1969    Hoover et al.
(Continued)

OTHER PUBLICATIONS

Barascav D, Halliburton, retrieved Aug. 19, 2014 from http://www.halliburton.com/public/bar/contents/Data_Sheets/web/Product_Data_Sheets/A_through_C/BARASCAV_D.PDF, dated May 19, 2010.*

*Primary Examiner* — Angela M DiTrani
(74) *Attorney, Agent, or Firm* — Pate Baird, PLLC

(57) ABSTRACT

A method for improving hydraulic fracturing creates coated proppants containing one or more chemical constituents bonded to a substrate and introduced into the fracturing fluid itself. The substrate that eventually acts as a proppant may be sand, ceramic, resin coated sand, and other materials. Typically, the materials that are coated as powders adhered to the substrate may include friction reducers, biosides, oxygen scavengers, clay stabilizers, scale inhibitors, gelling agents, or the like. By adhering solid materials to a substrate 12 by a binder 14, a single, solid, granular material may be maintained onsite, requiring reduced footprint, reduced mixing and may introduce almost instantaneously into a fracturing flow stream all the necessary chemical constituents, which will eventually become mixed. The result is reduced time, energy, manpower, equipment, and space at the sight, while reducing the environmental impact of transportation, spills, hydrocarbon use, and the like.

14 Claims, 10 Drawing Sheets

(56) References Cited

U.S. PATENT DOCUMENTS

| | | | |
|---|---|---|---|
| 3,752,233 | A | 8/1973 | Svaldi et al. |
| 3,768,565 | A | 10/1973 | Persinski et al. |
| 3,841,402 | A | 10/1974 | Knight et al. |
| 3,868,328 | A | 2/1975 | Boothe et al. |
| 3,943,060 | A | 3/1976 | Martin et al. |
| 4,195,010 | A | 3/1980 | Russell et al. |
| 4,247,331 | A | 1/1981 | Hamlin et al. |
| 5,806,593 | A | 9/1998 | Surles |
| 7,135,231 | B1 | 11/2006 | Sinclair et al. |
| 7,156,194 | B2 | 1/2007 | Nguyen |
| 7,216,705 | B2 * | 5/2007 | Saini et al. ............. 166/279 |
| 7,334,640 | B2 | 2/2008 | Hanes, Jr. et al. |
| 7,510,656 | B2 | 3/2009 | Shafer et al. |
| 7,527,736 | B2 | 5/2009 | Shafer et al. |
| 7,628,919 | B2 | 12/2009 | Shafer et al. |
| 7,722,770 | B2 | 5/2010 | Shafer et al. |
| 7,814,980 | B2 | 10/2010 | Bryant et al. |
| 7,888,297 | B2 | 2/2011 | Hanes, Jr. et al. |
| 8,354,360 | B2 | 1/2013 | Phatak |
| 2004/0244978 | A1 | 12/2004 | Shaarpour |
| 2006/0211580 | A1 | 9/2006 | Wang et al. |
| 2008/0045422 | A1 * | 2/2008 | Hanes et al. ............. 507/224 |
| 2008/0064614 | A1 | 3/2008 | Ahrenst et al. |
| 2008/0108524 | A1 * | 5/2008 | Willberg et al. ........... 507/225 |
| 2009/0065253 | A1 | 3/2009 | Suarez-Rivera et al. |
| 2010/0222242 | A1 | 9/2010 | Huang et al. |
| 2010/0248997 | A1 | 9/2010 | Li et al. |
| 2010/0307749 | A1 * | 12/2010 | Nguyen et al. ............ 166/278 |
| 2011/0017677 | A1 | 1/2011 | Evans |
| 2011/0098377 | A1 | 4/2011 | Huang et al. |
| 2011/0120719 | A1 * | 5/2011 | Soane et al. ............ 166/308.1 |
| 2011/0245113 | A1 | 10/2011 | Phatak |
| 2011/0245114 | A1 | 10/2011 | Gupta et al. |
| 2012/0080192 | A1 * | 4/2012 | Hendrickson et al. ..... 166/308.1 |
| 2012/0190593 | A1 | 7/2012 | Soane et al. |
| 2012/0214714 | A1 * | 8/2012 | Whitwell et al. ........... 507/222 |
| 2012/0225800 | A1 * | 9/2012 | Hendrickson ............. 507/211 |
| 2012/0305254 | A1 | 12/2012 | Chen et al. |
| 2013/0161003 | A1 | 6/2013 | Makarychev-Mikhailov et al. |
| 2013/0233545 | A1 * | 9/2013 | Mahoney et al. .......... 166/280.2 |

* cited by examiner

HYDRAULIC FRACTURE COMPOSITION AND METHOD

RELATED APPLICATIONS

This application is a continuation-in-part of U.S. patent application Ser. No. 13/299,288, filed Nov. 17, 2011, which is a continuation-in-part of U.S. patent application Ser. No. 12/789,177, filed May 27, 2010, which is a continuation of U.S. patent application Ser. No. 12/324,608, now U.S. Pat. No. 7,726,070, issued Jun. 1, 2010 to Thrash, which claims the benefit of U.S. Provisional Patent Application Ser. No. 61/012,912, filed on Dec. 11, 2007.

BACKGROUND

1. The Field of the Invention

This invention relates to oil field and oil well development, and, more particularly, to novel systems and methods for fracturing and propping fissures in oil-bearing formations to increase productivity.

2. The Background Art

Oil well development has over one hundred years of extensive engineering and chemical improvements. Various methods for stimulating production of well bores associated with an oil reservoir have been developed. For example, United States Patent Application Publication US 2009/0065253 A1 by Suarez-Rivera et al. and entitled "Method and System for Increasing Production of a Reservoir" is incorporated herein by reference in its entirety and provides a description of fracturing technology in order to increase permeability of reservoirs. Moreover, various techniques exist to further improve the fracture channels, such as by acid etching as described in U.S. Pat. No. 3,943,060, issued Mar. 9, 1976 to Martin et al., which is likewise incorporated herein by reference in its entirety.

In general, different types of processes require various treatments. In general, well production can be improved by fracturing formations. Fracturing is typically done by pumping a formation full of a fluid, containing a large fraction of water, and pressurizing that fluid in order to apply large surface forces to parts of the formation. These large surface forces cause stresses, and by virtue of the massive areas involved, can produce extremely high forces and stresses in the rock formations.

Accordingly, the rock formations tend to shatter, increasing porosity an providing space for the production oil to pass through the formation toward the bore hole for extraction. However, as the foregoing references describe, the chemistry is not simple, the energy and time required for incorporation of various materials into mixtures is time, money, energy, and other resource intensive.

It would be an advance in the art if such properties as viscosity, absorption, mixing, propping, and so forth could be improved by an improved composition and method for introduction.

Moreover, hydraulic fracturing has a rather sophisticated process for adding various constituents to the fracking fluids. Not only must proppants be added, but various other chemicals. In certain fracturing processes, it has been found important or even necessary to blend materials into the working fluid for fracturing. Such blending requires substantial equipment, occupying a very significant footprint on the overall well site.

Moreover, this equipment requires manpower, and maintenance of numerous receiving and storage areas. These are needed for various constituent products that will ultimately be added to the working fluid. All of these processes for mixing auxiliary materials into the fluid cause delays in time, since many of the materials require substantial mixing.

Particularly with small particles, surface tension tends to float such materials on the of liquids and require substantial mixing and substantial associated time. Many solids must be pre-mixed in oils, emulsions, and the like, increasing the effect of any spill. Meanwhile, addition of chemicals to a fracturing flow necessarily creates uneven distributions of additives. For example, upon addition, into the flow, a constituent is at a very high concentration near the well head. Meanwhile, none of that newly added constituent exists elsewhere. Thus, the ability to thoroughly distribute material, or to even get it distributed well throughout the fluid being introduced, has proven difficult.

Similarly, transportation of individual constituent chemicals and materials to the well site requires multiple vehicles specialized to different types of materials and phases. For example, some materials are fluids, some are solids, some use a water solvent, some use a petroleum-based solvent, and such materials must be hauled, delivered, and handled in distinct ways with their own suitable storage, handling, and transport equipment.

Various complaints have been encountered with the amount of hydrocarbons, such as various emulsions, chemical additives, including such materials as diesel fuel and the like that are often used. With such liquid chemicals on site, the risk of surface contamination due to chemical spills of such materials is increased. Even when contained in smaller containers, such materials run the risk of spills, carrying about by water, wind, and other weather, as well as the prospect of possible spilling during delivery, handling, or the feeding and mixing processes.

Meanwhile, the operational footprint required for storage, mixing systems, receiving, shipping, and the like increase the overall operational footprint of a well site. Moreover, money, labor, and time are substantial for the process of receiving, preparation, storage, handling, and ultimately mixing materials that will be added to a fracturing fluid.

Thus, it would be a substantial advance in the art to provide a system and method, and particularly a material, that would eliminate many of the handling, equipment, footprint, transportation, and other problems that exist in prior art materials and mixing systems to service fracture fluids.

BRIEF SUMMARY OF THE INVENTION

In view of the foregoing, in accordance with the invention as embodied and broadly described herein, a method, apparatus, and composition are disclosed in certain embodiments in accordance with the present invention, as including a substrate that may be formed of sand, rock product, ceramic sand, gravel, or other hard and structurally strong materials, provided with a binder to temporarily or permanently secure a hydrating polymer in proximity to the substrated. When used herein any reference to sand or proppant refers to any or all of these used in accordance with the invention. In certain embodiments of a method in accordance with the invention, a composition as described may be mixed directly into drilling fluids, such as a fracturing fluid made up of water and other additives.

By virtue of the increased surface area and weight provided to the polymeric powders affixed to the substrate, the surface area, and consequently the frictional drag, is greatly increased, sweeping the material of the invention into a flow of fluid. This greatly decreases the time required to absorb polymers into the fluid.

In fact, rather than having to wait to have the polymers thoroughly mixed, or absorb a full capacity of water, and thereby flow properly with the drilling fluid or fracturing fluid, a composition in accordance with the invention will sweep along with the fluid immediately, with the weight of the substrate submerging the polymer. Meanwhile, the cross sectional area presented results in hydrodynamic drag sweeps the composition along with the flow.

Meanwhile, over time, the polymeric powder adhered to the substrate will absorb water, without the necessity for the time, energy, temperature, mixing, and so forth that might otherwise be required by surface mixing. Thus, the composition in accordance with the invention is immediately transportable and flows, relying on the drilling or fracturing fluid as its carrier.

Moreover, as the polymer tends to pick up more water, the density of the granule of substrate and polymer powder becomes closer to the density of water. Accordingly, the size increase and the density change tend to drive the particles of the composition even more homogeneously with the flowing fluid. Thus, the sand does not settle out in various eddies, obstructions, and other locations of low velocity. Rather, the sand continues to be carried with the fluid, providing a double benefit. That is, the sand weight and area helps to initially mix and drive the particles (granules) with the fluid. Thereafter, the hydration of the polymer tends to increase the surface area and reduce the density of the granule or particle, tending to make the particles flow even better and more homogeneously with the surrounding fluid.

Ultimately, as the particles (granules) of the composition flow into fracture locations, they provide very small proppants as the substrate, such as sand, becomes trapped and lodged at various choke points. Nevertheless, because of the small size, the sand or other substrate acting as a proppant, simply needs to provide an offset, keeping fractured surfaces from collapsing back against one another. By providing the small, strong points of separation, the substrate provides a well distributed proppant, carried to maximum extent that the fluids will travel, and deposited in various traps, choke points, and the like.

The net saving in time, money, energy for heating and pumping, and the like is significant. Meanwhile, various technologies for reducing friction in the flow of fluid pumped into bore holes and other formation spaces is described in several patents, including U.S. Pat. No. 3,868,328, issued Feb. 25, 1975 to Boothe et al. and directed to friction reducing compounds, as well as U.S. Pat. No. 3,768,565, issued Oct. 30, 1973 to Persinski et al. and directed to friction reducing, U.S. Patent Application Publication US 2001/0245114 A1 by Gupta et al. directed to well servicing fluid, and U.S. Patent Application Publication US 2008/0064614 A1 by Ahrenst et al. and directed to friction reduction fluids, all described various techniques, materials, methods, and apparatus for developing, implementing, and benefiting from various well fluids. All the foregoing patent application publications and patents are hereby incorporated by reference.

Similarly, the development of various chemicals has been ubiquitous in oil field development. For example, U.S. Pat. No. 3,442,803, issued May 6, 1969 to Hoover et al. is directed to thickened friction reducers, discusses various chemical compositions, and is also incorporated herein by reference in its entirety.

In one embodiment of an apparatus, composition and method in accordance with the invention, a method may be used for formation fracturing. The formation may be in rock and within or near an oil reservoir underground. One may select an oil field region having a formation to be fractured. Fracturing may be sought to increase production. By providing a bore into the formation and a pump, a carrier material, typically comprising a liquid, and sometimes other materials dissolved or carried therein may be pumped into the formation through the bore.

The carrier as a liquid, or slurry comprising a liquid, or otherwise containing a liquid may be driven by the pump to be pressurized into the formation. However, the carrier may be provided an additive formed as granules. Each granule may include a substrate, such as a grain of sand, ceramic sand, crushed rock, other rock products, or the like having bonded thereto many particles (e.g., powder) formed from a polymer.

The polymer may be selected to have various properties, including lubricity, water absorption, water solubility, or the like. This hydrophilic polymer may be bonded permanently, temporarily, or the like to secure to the substrate. Various binders may be used alone or in combination. These may range from a solvent (e.g., organic or water) simply softening the polymer itself to bond it, to glues, sugars, molasses, and various other saccharides, as well as other products, including starches, other polymers, and so forth.

Thus, with some bonds, the polymer powder may be less permanent or attached to have a bond that is less robust. Over time, the polymer powder so attached may wear off, pull away, or otherwise remove from the substrate into the carrier fluid, and may even act as a viscous agent, lubricant, or the like in the carrier.

The method may include introducing the additive directly into the carrier. The more dense substrate will immediately submerge the granules in the carrier at ambient conditions. Thus heating, extensive mixing, waiting, and the like may be dispensed with, as the granules typically will not float or resist mixing once initial surface tension is broken.

Pumping the carrier toward the formation is possible immediately. The carrier fluid carries the granules by the liquid dragging against the substrate (with the particles of polymer attached. The substrate's cross sectional area engages immediately the surrounding liquid, dragging it into the carrier to flow substantially immediately therewith.

Meanwhile, weighting, by the substrate of the polymer, permits the granules to flow into and with the carrier independently from absorption of any of the liquid into the polymer. Nevertheless, over time, absorbing by the polymer a portion of the liquid results in the polymer expanding and providing by the polymer, lubricity to the carrier with respect to the formation;

Creating fractures may be accomplished by pressurizing the carrier in the formation. This creates fissures or fractures. Thus, flowing of the carrier and particles throughout the fractures or fissures in the formation results in lodging, by the particles, within those fractures or fissures. Unable to realign, adjacent surfaces of rock, now fracture cannot close back together due to propping open the fractures by the substrate granules lodging in the fractures.

The substrate is best if selected from an inorganic material, such as sand, ceramic sand, or other hard, strong, rock product. The polymer may be selected from natural or synthetically formulated polymers. For example polymers of at acrylic acid, acrylate, and various amides are available. Polyacrylamide has been demonstrated suitable for all properties discussed above.

In fracturing a rock formation, the method may include providing an additive comprising a substrate formed as granules, each having an exterior surface, particles formed of a hydrophilic material, the particles being comminuted to a size smaller than the size of the granules and having first and second sides comprising surfaces. The granules may each be coated with the particles, the particles being dry and bonded to the exterior surface by any suitable binder, including the polymer softened with a solvent. The particles are each secured by the first side to the granules, the second side extending radially outward therefrom.

Upon identifying a reservoir, typically far underground from thousands of feet to miles, perhaps, and extending in a formation of rock, one needs to provide a bore into the formation. Providing a carrier, comprising a liquid, and possibly other materials known in the art, is for the purpose of fracturing the formation. Introducing the additive directly into the liquid at ambient conditions is possible, because the substrate weighs the granules down, and there is no need for long mixing, heating or the like as in addition of polymers directly to the carrier.

Thus, pumping may continue or begin immediately to move the carrier and additive down the bore and toward the formation. This results in exposing the second sides of the polymer powder particles directly to the liquid during transit of the carrier and additive toward and into the formation. The polymer particles thus begin absorbing, a portion of the liquid, typically principally water. Swelling of the polymer increases the size, effective diameter, and cross-sectional area, thus increasing the fluid drag on the granules.

Fracturing, typically by hydraulic pressure in the carrier creates fissures in the formation by fracturing the rock pieces in bending, or by layer separation, with tensile stresses breaking the rock. The resulting fissures allow carrying, by the carrier, of the granules into the fissures. However, fissures vary in size and path, resulting in lodging of granules, within the fissures. The granules do not settle out from the carrier, and thus may travel far into the formation and every fissure. However, each time a grain or granule is lodged like a chock stone, it obstructs the ability of the adjacent rock surfaces to close back with one another.

Thus, rather than the proppant (substrate) settling out ineffectually, failing to prop open the fissures, the granules are swept forcefully with the flow of the carrier wherever the carrier can flow, until lodged. Meanwhile, the lubricity of the polymer aids the granules, and thus the substrate from being slowed, trapped, or settled out by the slow flowing boundary layer at the solid wall bounding the flow.

In summary, weighting, by the substrate, sinks the polymer into the carrier readily and independently from absorption of the liquid into the polymer. Mixing, dissolving, and so forth are unnecessary, as the substrate drags the polymer into the carrier, and the carrier drags the granule along with it in its flow path. Lubrication is provided by the polymer between the substrate of each granule and adjacent solid walls of the bore, passages previously existing in the formation, and the fissures formed by fracturing. Any separating, by some of the powdered polymer particles from the substrate, still reduces friction drag on passage of the carrier and particles within the formation.

A composition for fracturing and propping a formation of rock may include a fluid operating as a carrier to be pumped into a rock formation, a substrate comprising granules of an inorganic material, each granule having an outer surface and a size characterized by a maximum dimension thereacross, and all the granules together having an average maximum dimension corresponding thereto. A polymer comprising a hydrophilic material selected to absorb water in an amount greater than the weight thereof may be bound to the substrate. The polymer is comminuted to particles, each particle having a size characterized by a maximum dimension thereacross.

All the polymer particles may be characterized by an average maximum dimension, and an effective (e.g., hydraulic diameter). The average maximum dimension of the particles is best if smaller, preferably much smaller, than the average maximum dimension of the granules.

The particles of the polymer, bound to the substrate, will travel with it in the fluid. Particles of the polymer are thus further directly exposed to water in the fluid during travel with the fluid. The granules, flowing in the fluid, are carried by the hydrodynamic drag of the fluid against the cross-sectional area of the granules coated with the particles of the polymer. The polymer, selected to expand by absorbing water directly from the fluid, increases the area and drag, assisting distribution in the formation by the carrier fluid. The polymer meanwhile operates as a lubricant lubricating the motion of the substrate against the formation during flow of the granules against solid surfaces in the formation, bore, and fracture fissures.

The inorganic material, such as sand, ceramic sand, or the like is typically sized to lodge in fissures formed in the formation and has mechanical properties rendering it a proppant capable of holding open fissures formed in the formation. In certain embodiments, a water soluble binder is used, then a substrate may release additives into the fracturing fluid quickly or slowly after insertion in the working fluid.

A substrate may perform as a proppant, and may be constituted of sand, ceramic, another rock or mineral product, a resin coated, or other material used to prop open fractures. Such a substrate may be provided with a binder securing powdered components of suitable additives to be introduced into a fracturing fluid.

For example, a friction reducer, biocide, oxygen scavenger, clay stabilizer, scale inhibitor, gelling agent, or the like may be included in a mix, or as an element to be adhered to a substrate proppant. The substrate thereby forms particles that will easily be drawn into a flow of fracturing fluid, thus introducing all the necessary constituents into the flow. This occurs rapidly, without having to wait for mixing to occur topside on the site before introduction into the bore. Rather, mixing can take place and hydration or distribution in the flow may take place on the fly as the flow of fluid courses through the bore toward the formation. Thus, the preparation and introduction time on the surface at the well site is minimized.

In certain embodiments, the composition may be mixed directly into the fluid to form a complete and suitable fracturing fluid with all the necessary additives desired. By adhering chemicals to the proppant as the operable substrate, in the correct ratios, elaborate mixing ratios and elaborate mixing processes, and control thereof, as well as their related equipment, personnel, time, storage, and handling are greatly reduced, and optimally eliminated. Thus, the operational footprint of a service company on the well site is reduced, as well as the time, cost, labor, and so forth required to measure, add, mix, and otherwise introduce desired chemical constituents into the fracturing fluid.

By coating a proppant or substrate with the suitable materials (e.g., chemicals, etc.) an even mix of chemicals is maintained within the fracturing fluid much more easily. Moreover, distribution thereof within the flow is straightforward. In fact, all those additives may thereby all be present in exactly the proper ratios at all times at the time they are introduced. Thus, adding them one at a time, working with them to try to get them all introduced at about the same time, and so forth, as encountered in the prior art is no longer a problem.

Because many or all desired constituents may be coated onto a single substrate 12, or each granule of a single substrate, then numerous constituents, including previously dissolved liquids or solids that have been rendered liquid by introduction into solvents, in order to ensure more rapid mixing, may be reduced or eliminated. Thus the full array of constituent chemicals to be used as additives in the fluid may be provided with proppants in the delivery of a single material, granular in nature, solid in phase, and simple to be stored, transported, handled, and the like. Thus, emissions, spills, other environmental risks, may be reduced or eliminated.

By using powdered base chemicals, the carriers or solvents that were previously needed, often hydrocarbon based emulsions and the like, may be eliminated. Thus, the risk of surface spills and consequent contamination may be reduced or eliminated.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

Figure 1:
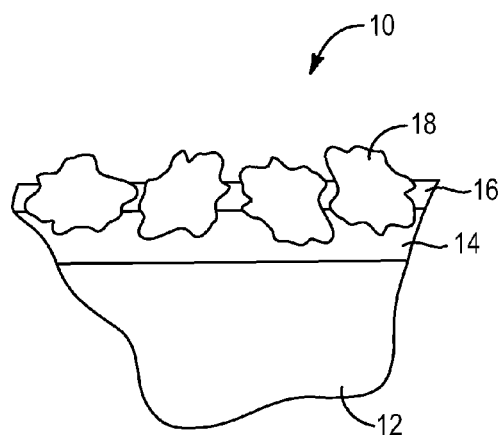
FIG. 1 is a schematic cross-sectional view of a material including a substrate provided with a binder securing a hydrating polymer thereto in accordance with the invention.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Referring to FIG. 1, a material 10 in accordance with the invention may include a substrate 12 formed of a suitable material for placement in the vicinity of a fracture region. For example, a substrate may be a particle of sand, ceramic sand, volcanic grit, or other hard material. In some embodiments, a substrate may be formed of organic or inorganic material. Nevertheless, it has been found effective to use sand as a substrate 12 inasmuch as it is submersible in water and will not float as many organic materials will when dry. Likewise, the sand as substrate 12 is comminuted to such a small size that interstices between individual grains of the sand substrate 12 provide ample space and minimum distance for water to surround each of the substrate 12 particles.

In the illustrated embodiment, a binder 14 may be distributed as a comparatively thin layer on the surface of the substrate 12. Typical materials for binders may include both temporary and permanent binders 14. Permanent binders include many polymers, natural and synthetic. Temporary binders may be sugar-based or other water soluble materials. For example, corn syrup, molasses, and the like may form temporary binders. In the presence of water, such material may ultimately dissolve. Nevertheless, so long as the substrate 12 is not turned, mixed, or otherwise disturbed significantly, any other materials supported by the binder 14 would not be expected to dislocate.

Otherwise, certain naturally or synthetically occurring polymers may also be used as a binder 14. Lignicite may be used as a binder 14. Lignicite is a byproduct of wood, and provides material having good adhesive properties, and substantial permanence as a binder 14 on a substrate 12. Any suitable insoluble polymer may be used for more permanent binding.

Other polymers may be used to form a binder 14. For example, various materials used as glues, including mucilage, gelatin, other water soluble polymers including, for example, ELMER'S™ glue, and the like may also operate as binders 14 to bind materials to a substrate 12.

In certain embodiments, the substrate 12 may be used in oil fields as a substrate 12 for polymer additives to fracture fluids. In other situations, the substrate 12 may be implemented as a proppant.

Pigment 16 may be implemented in any of several manners. For example, the substrate 12 may have pigment 16 applied prior to the application of the binder 14. In alternative embodiments, the pigment 16 may actually be included in the binder 14, which becomes a pigmented coating on the substrate 12. In yet other embodiments, the pigments 16 may be added to a hydration particle 18 either as a pigment 16 mixed therein, or as a pigment 16 applied as a coating thereto. Thus the location of the pigment 16 in the Figures is schematic and may take alternative location or application method.

Particles 18 of a hydrophilic polymer material may be bonded to the substrate 12 by the binder 14. Particles may be sized to substantially coat or periodically coat the substrate 12.

In certain embodiments, the hydrophilic material 18 may be a powdered polymeric material 18 such as polyacrylamide or any of the materials in the patent documents incorporated by reference. In other embodiments, the particles 18 may actually be organic material having capillary action to readily absorb and hold water. In one presently contemplated embodiment of an apparatus in accordance with the invention, the particles 18 may be powdered polymeric material in a dehydrated state, and having a capacity to absorb water, typically many times the weight (e.g., five to forty times) of a particular particle 18.

The substrate 12, in certain embodiments, may be some form of sand or granular material. The sand will typically be cleaned and washed to remove dust and organic material that may inhibit the binder 14 from being effective. Likewise, the substrate 12 may be sized of any suitable size. For example, sand particles may range from much less than a millimeter in effective diameter or distance thereacross to approximately two millimeters across. Very coarse sands or ceramic sands may have even larger effective diameters. Hydraulic diameter is effective diameter (four times the area divided by the wetted perimeter). However, in one presently contemplated embodiment, washed and dried sand such as is used in construction, such as in concrete, has been found to be suitable. Fine sands such as masonry sands tend to be smaller, and also can function suitably in accordance with the invention.

Accordingly, the distance across each powder particle 18 may be selected to provide an effective coating of powdered particles 18 on the substrate 12. In one presently contemplated embodiment, the effective diameter of the particles 18 may be from about a 30 mesh size to about a 100 mesh size. For example, a sieve system for classifying particles has various mesh sizes. A size of about 30 mesh, able to pass through a 30 mesh sieve, (i.e., about 0.6 mm) has been found suitable. Likewise, powdering the particles 18 to a size sufficiently small to pass through a 100 mesh (i.e., about 0.015 mm) sieve is also satisfactory. A mesh size of from about 50 mesh to about 75 mesh is an appropriate material to obtain excellent adhesion of particles 18 in the binder 14, with a suitable size of the particles 18 to absorb significant liquid at the surface of the substrate 12.

As a practical matter, about half the volume of a container containing a substrate 12 as particulate matter will be space, interstices between the granules of the substrate 12. One advantage of using materials such as sand as the substrate 12 is that a coating of the particles 18 may provide a substantial volume of water once the particles 18 are fully saturated. By contrast, where the size of the particles 18 is too many orders of magnitude smaller than the effective diameter or size of the substrate particles 12, less of the space between the substrate particles 12 is effectively used for storing water. Thus, sand as a substrate 12 coated by particles 18 of a hydrophilic material such as a polymer will provide substantial space between the substrate particles 12 to hold water-laden particles 18.

The diameter of the particles 18, or the effective diameter thereof, is typically within about an order of magnitude (e.g., 10×) smaller than the effective diameter of the particles of the substrate 12. This order of magnitude may be changed. For example, the order of magnitude difference less than about 1 order of magnitude (i.e., 10×) may still be effective. Similarly, an order of magnitude difference of 2 (i.e., 100×) may also function.

However, with particles 18 too much smaller than an order of magnitude smaller than the effective diameter of the substrate 12, the interstitial space may not be as effectively used. Likewise, with an effective diameter of particles 18 near or larger than about 1 order of magnitude smaller than the size of the particles of the substrate 12, binding may be less effective and the particles 18 may interfere more with the substrate itself as well as the flow of water through the interstitial spaces needed in order to properly hydrate a material 10.

Figure 2:
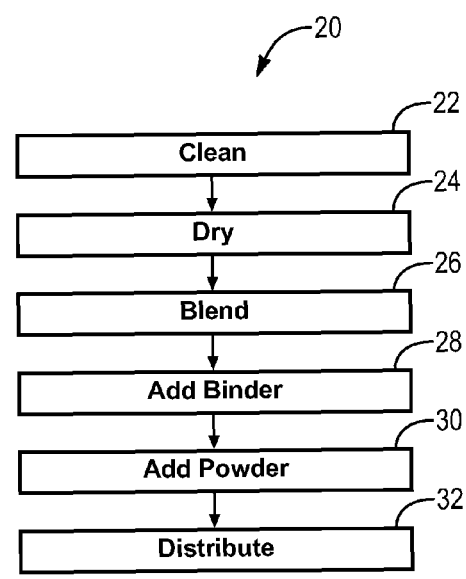
FIG. 2 is a schematic block diagram of one embodiment of a process for formulating and producing fluid additive particles in accordance with the invention.

Referring to FIG. 2, an embodiment of a process for formulating the material 10 may involve cleaning 22 the material of the substrate 12. Likewise, the material of the substrate 12 may be dried 24 to make it more effective in receiving a binder 14. The material of the substrate 12 may then be blended 26.

One embodiment, a ribbon blender provides an effective mechanism to perform continuous blending as the binder 14 is added 28. Other types of mixers, such as rotary mixers, and the like may be used. However, a ribbon blender provides a blending 26 that is effective to distribute binder 14 as it is added 28.

For example, if an individual particle of the substrate 12 receives too much binder 14, and thus begins to agglomerate with other particles of the substrate 12, a ribbon binder will tend to separate the particles as a natural consequences of its shearing and drawing action during blending 26.

As the binder 14 is added 28 to the mixture being blended 26, the individual particles of the substrate 12 will be substantially evenly coated. At this stage, the binder 14 may also be heated in order to reduce its viscosity and improve blending. Likewise, the material of the substrate 12 or the environment of the blending 26 may be heated in order to improve the evenness of the distribution of the binder 14 on the surfaces of the substrate 12 materials or particles 12.

Blending 26 of the binder 14 into the material of the substrate 12 is complete when coating is substantially even, and the texture of the material 10 has an ability to clump, yet is easily crumbled and broken into individual particles. At that point, addition 30 of the hydrophilic particles 18 may be accomplished.

For example, adding 30 the particles 18 as a powder into the blending 26 is a naturally stable process. Typically the particles 18 attach to the binder 14 of the substrate 12 particles, thus removing from activity that location. Accordingly, other particles 18 rather than agglomerating with their own type of material will continue to tumble in the blending 26 until exposed to a suitable location of binder 14 of the substrate 12. Thus, the adding 30 of the particles 18 or powder 18 of hydrophilic material will tend to be a naturally stable process providing a substantially even coating on all the particles of the substrate 12.

Just as marshmallows are dusted with corn starch, rendering them no longer tacky with respect to one another, the material 10 formulated by the process 20 are dusted with particles 18 and will pour freely. Accordingly, distribution 32 may be conducted in a variety of ways and may include one or several processes. For example, distribution may include marketing distribution from packaging after completion of blending 26, shipping to distributors and retailers, and purchase and application by users.

An important part of distribution 32 is the deployment of the material 10. In one embodiment of an apparatus and method in accordance with the invention, the material 10 may be poured, as if it were simply sand 12 or other substrate 12 alone. Since the powder 18 or particles 18 have substantially occupied the binder 14, the material 10 will not bind to itself, but will readily pour as the initial substrate material 12 will.

The material 10 may typically include from about 1 percent to about 20 percent of a hydrophilic material 18 or particles 18. The particles 18 may be formed of a naturally occurring material, such as a cellulose, gelatin, organic material, or the like.

In one embodiment, a synthetic gel, such as polyacrylamide may be used for the particles 18, in a ratio of from about 1 to about 20 percent particles 18 compared to the weight of the substrate 12. In experiments, a range of from about 5 to about 10 percent has been found to be the most effective for the amount particles 18.

Sizes of particles 18 may range from about 20 mesh to smaller than 100 mesh. Particles 18 of from about 50 to about 75 mesh have been found most effective.

The binder 14 may typically be in the range of from about in ¼ percent to about 3 percent of the weight of the substrate 12. A range of from about ¾ percent to about 1½ percent has been found to work best. That is, with a binder such as lignicite, ¼ of 1 percent has been found not to provide as reliable binding of particles 18 to the substrate 12. Meanwhile, a ratio of higher than about 3 percent by weight of binder 14 to the amount of a substrate 12, such as sand, when using lignicite as the binder 14, tends to provide too much agglomeration. The pouring ability of the material 10 is inhibited as well as the blending 26, due to agglomeration. Other binders also operate, including several smaller molecules that are water soluble. For example, glues, gelatins, sugars, molasses, and the like may be used as a binder 14. Insoluble binders are also useful and more permanent.

One substantial advantage for the material 10 in accordance with the present invention is that the material remains flowable as a sand-like material 10 into the fluids to be used in oil field fracturing. Thus, handling and application is simple, and the ability of granular material 10 to flow under and around small interstices of fractures provides for a very effective application.

Figure 3:
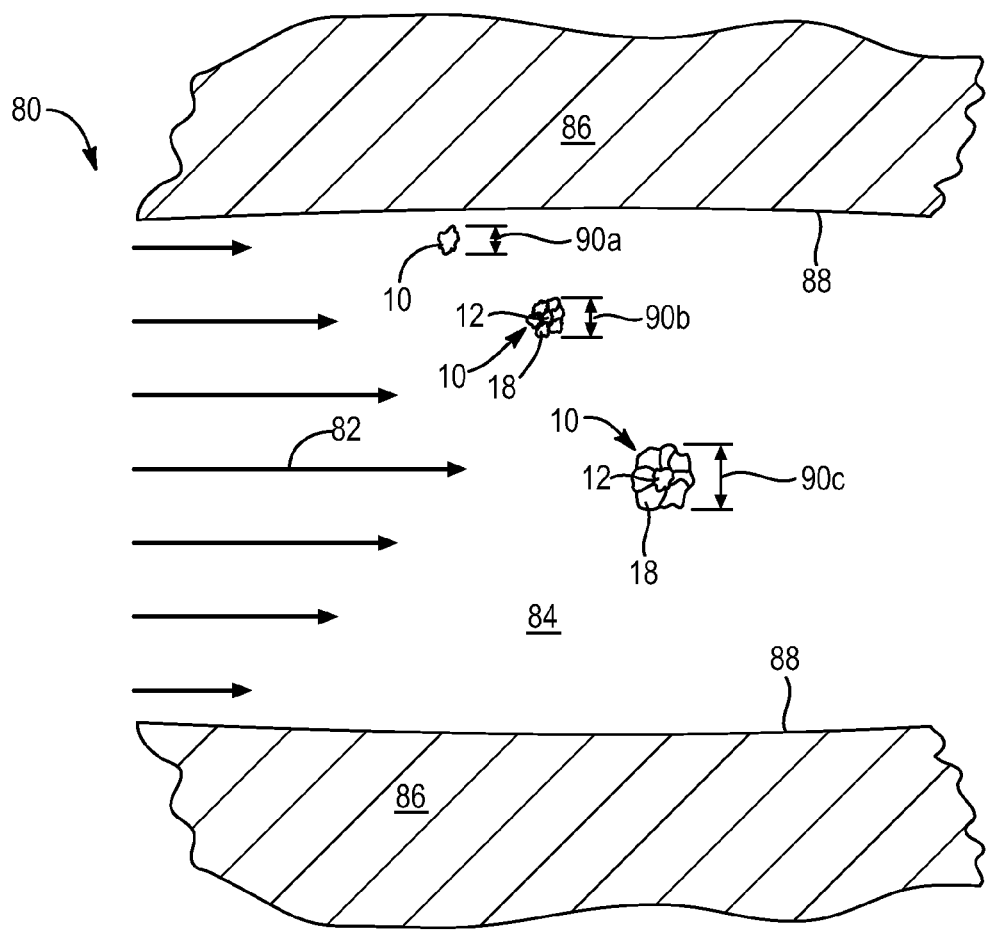
FIG. 3 is a schematic diagram of the fluid-particle interaction in an apparatus, composition, and method in accordance with the invention.

Referring to FIG. 3, a formation 80 such as a reservoir area of an oil may increase large and small flows 82 in passages 84 formed in the rock 86 of the formation 80. Typically, the flow 82 represented by arrows 82 indicating the development of flow at a faster speed in center of a passage 84, and the lower velocity near the wall 88 of the passage 84, illustrates the flow 82 of fluid in the passage 84.

In the illustrated embodiment, the granules 10 or large composite particles 10 or the materials 10 formed as a granulated material 10, having the substrate 12 in the center column with the polymer 18 adhered by a binder 12 on the outside thereof. This material 10 may be added to a flow 82 being pumped into a formation 80. Initially, a particle 10 will have an effective diameter 90a. In this condition, the particle 10 of material 10 is largely dependant on the density of the substrate 12, which constitutes the majority of its volume. Eventually, over time, with exposure to the liquid 82 or flow 82 and the water of that flow 82, the polymer 18 will absorb water, increasing in its effective diameter 90b. Ultimately, the polymer 18 or the polymer powder 18 will eventually become fully hydrated, increasing many times its size, and beginning to dominate the effective diameter 90c or hydraulic diameter 90c of the particle 10.

Initially, the diameter 90a reflects the comparatively smaller size and larger density of the particle 10 dominated by the weigh of the substrate 12, such as sand, ceramic sand, or some other hard and strong material. Ultimately, the diameter 90a or effective diameter 90a is sufficient to provide fluid drag according to fluid dynamic equations, drawing the particle 10 into the flow 82.

Meanwhile, the increase in diameter 90b and the ultimate effective diameter 90c result in reduction of the density of the particle 10 as the polymer 18 absorbs more water, bringing the net density of the particle 10 closer to the density of water. Accordingly, the particles 10 flow with the water exactly in sync, so to speak, rather than settling out as a bare substrate 12 would do.

For example, in areas where eddies in the flow occur, such as corners, crevices, walls, and the like, heavy materials having higher density, such as sand and the like, normally will tend to drift out of the flow, toward a wall 88, and ultimately will settle out. Instead, by virtue of the large "sail" presented by the larger diameter 90c of a fully hydrated polymer 18, each particle 10 stays with the flow 82 in passage 84, providing much more effective transport.

Figure 4:
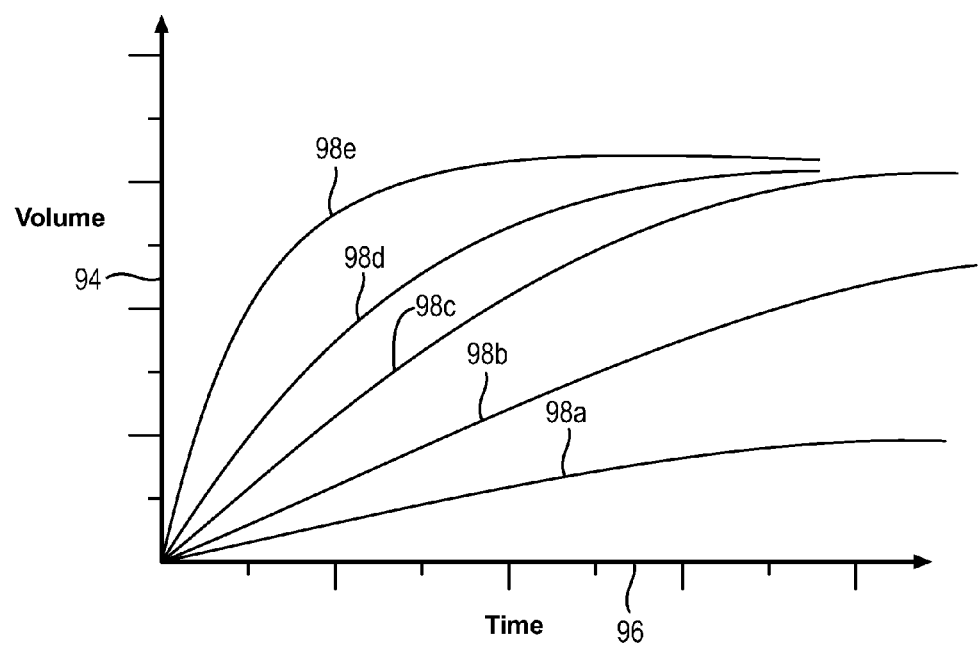
FIG. 4 is a chart illustrating qualitatively the relationship between volumetric increase over time at various temperatures, illustrating the improved activation with minimum mixing and temperature increase of particles in accordance with the invention.

Referring to FIG. 4, a chart 92 illustrates a volume axis 94 representing the volume of a particle 10 or material 10 in accordance with the invention. The volume axis 94 is displayed orthogonally with respect to a time axis 96, representing the passage of time of the particle 10 submerged in a carrier 82 or flow 82 of fluid 82. Typically, at different temperatures, illustrated by curves 98a-98e, with the temperature associated with curve 98a being the coldest and the temperature associated with the curve 98e being the hottest, one can visualize how heat added to a fluid flow 82 tends to increase the chemical activity and thus the rate of absorption of water into a polymer 18.

In an apparatus and method in accordance with the invention, the particles 10 may be added directly to a flow 82, without waiting for any significant time to absorb water into the polymer 18. Instead, the normal flow 82 will draw the particles 10 along in a passage 84 while exposing each individual particle 10 to surrounding fluid 82, thus promoting maximum rates of exposure and increased rates of absorption. Accordingly, the volume 94 increases, representing an increase in the absorption of water into the polymer 18.

In an apparatus and method in accordance with the invention, the curve 98a is suitable because the entire travel within the well bore, and within the formation 80 by the fluid 82 bearing the particles 10 is permissible and available as absorption time. By contrast, prior art systems rely on the increased temperature of curve 98e in order to provide the time, temperature, and mixing to work polymers into a flow 82 or liquid carrier 82.

Figure 5:
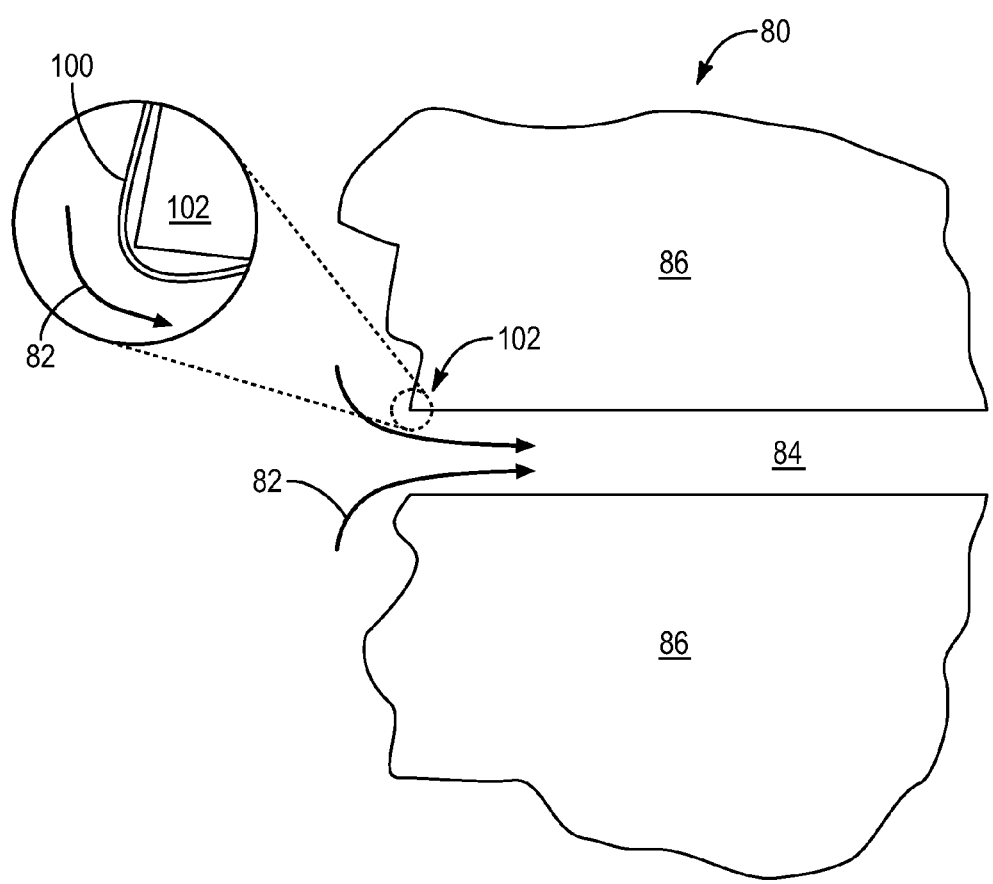
FIG. 5 is a schematic diagram illustrating one embodiment of friction reducing by polymers used in compositions in accordance with the invention.

Referring to FIG. 5, in one embodiment of an apparatus, composition, and method in accordance with the invention, some of the polymer 18 may eventually be scraped, sheared, or otherwise removed from the particles 10. If bonded only by itself with a water solvent, such a separation may be easier than if bonded by a more durable polymer. Such a release may even be engineered, timed, controlled by a solvent, or the like.

Thus, a certain amount of the polymer 18 may be released from the granule 10 into the carrier fluid 82 to flow with the fluid 82 and operate as a general friction reducer or provide its other inherent properties to the carrier fluid 82. By an engineered process of bonding and un-bonding, the polymer powder may be less permanent or attached to have a bond that is less robust. Over time, the polymer powder so attached may release, tear, wear off, pull away, or otherwise remove from the substrate into the carrier fluid to act as a viscosity agent, surfactant, lubricant, or the like in the carrier, according to its known properties available for modifying the carrier 82.

For example, a polymer 100 or polymer chain 100 may be captured on a corner 102 defining a passage 84 into which a flow 82 will proceed. Accordingly, the corner 102 renders less of an orifice on the passage 84 against entry of the flow 82 by virtue of the friction reduction of the polymer 100 in the fluid, deposited temporarily or permanently about a corner 102. Thus, other particles 10 passing the corner 100 may shear off a portion of the polymer 18 carried thereby or may rely on the presence of the polymer 18 as a direct friction reducing agent on the particle 10 (granule) itself, permitting the particles 10 to pass more easily with the flow 82 into the passage 84.

Figure 6A:
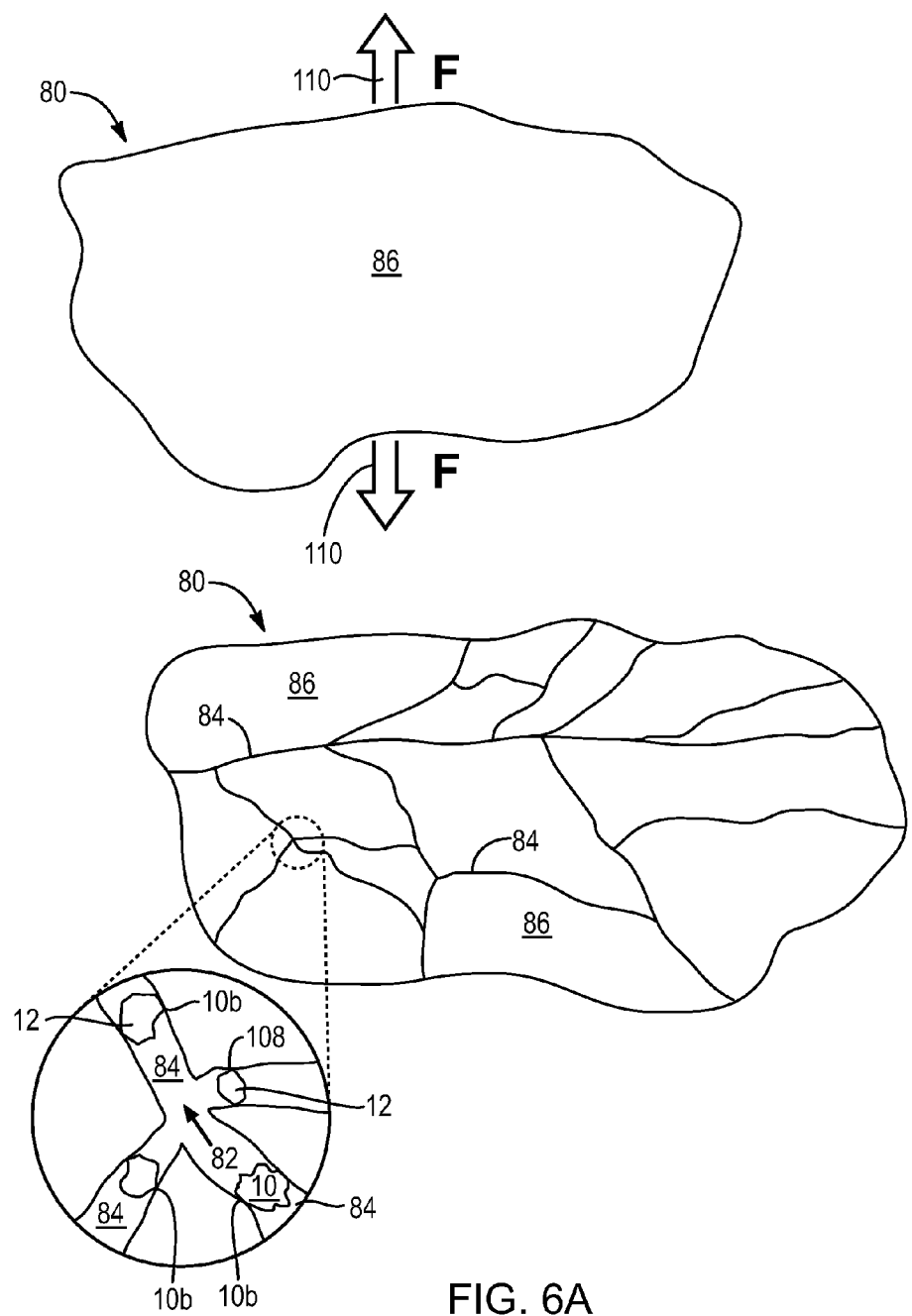
FIG. 6A is a schematic diagram of the fracturing and proppant action of particles in accordance with a method and composition according to the invention.
Figure 6B:
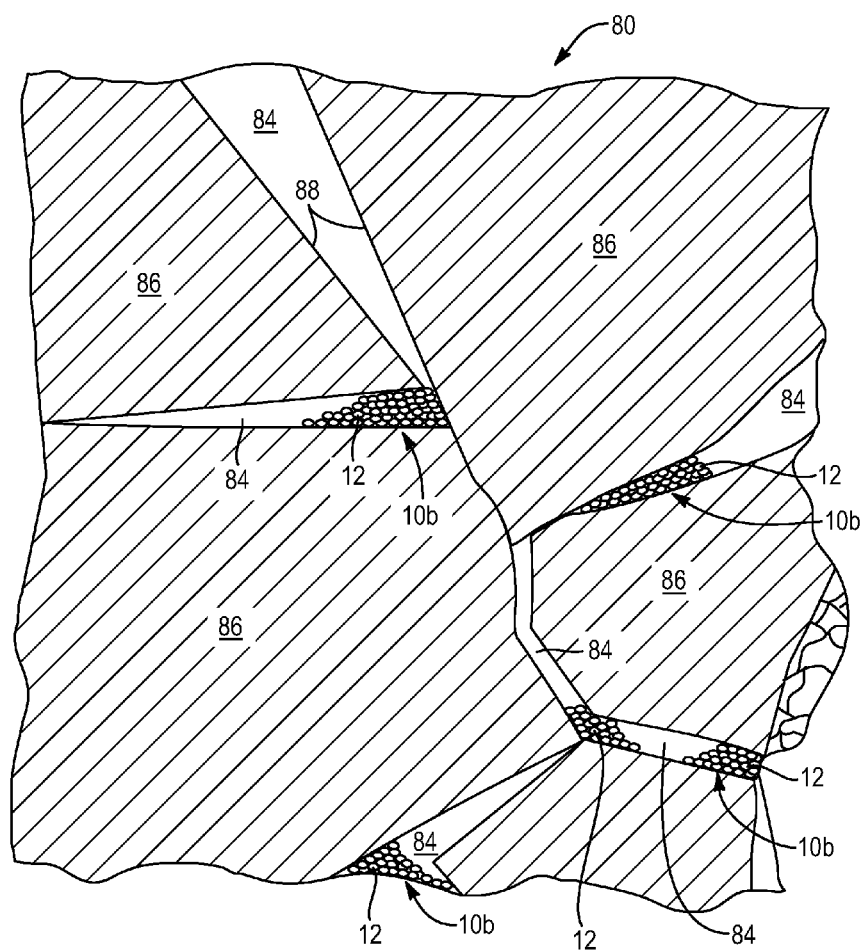
FIG. 6B is a schematic diagram illustrating a collection of proppant particles positioning rock fragments in a formation away from one another in order to maintain open passages in the formation.

Referring to FIGS. 6A and 6B, various fracture processes are described in various literature, including U.S. Patent Application publication US 2009/0065253 by Suarez-Rivera et al. incorporated herein by reference. In a fracturing process, the pressure 110 or force 110 applied to a formation 80 tends to force apart large expanses of rock. As a result of that expansion of passages 84 in a rock formation 80, the rock is stressed. Pressure pumped into the fluid 82 flowing in the passages 84 within the formation 80 results in bending stresses, tensile stresses, and so forth in the formation 80.

In FIG. 6A, the forces 110 illustrated the effect of a large pressure applied over a large area. Since pressure multiplied by area equals force, applying an elevated hydraulic pressure to a large surface of a rock 86 or rock segment 86 within a formation 80 results in tensile forces. Compressive forces will not tend to break rock. However, a tensile force, which may be induced by bending, expansion, or the like, results in fracture of the rock. The fracture of the rock 86 thus results in condition shown in the lower view, in which the passages 84 are mere fissures within the rock 86.

The inset of FIG. 6A magnifies the fissures 84 or passages 84 formed in the rock 86 and immediately entered by the working fluid 82 being used for the fracture. Having the particles 10 formed around substrates 12, the fluid 82 extends into each of the fissures formed. Fissures 84 are simply passages 84. Some may be large, others small.

Referring to FIG. 6B, proppants 10 trapped in a small location still displace a large amount of fractured rock 86. Thus, a small displacement at one location may still maintain opened another opening much larger elsewhere near the rock 86. The particles 10, even if as small as sand, may also collect and fill larger dead ends, slow flowing, and eddying spaces, eliminating the ability for rocks 86 to return to former positions.

After fracturing rock 86 to form all of the fissures 84, the fluid 82 will pass through the fissures, carrying particles 10, which eventually collect in cavities or reach choke points. In the absence of the particles 10, fissures 84 could close back up after the fracturing water leaves. However, by containing additives 18, and then losing them, the individual substrates 12 are themselves rock in the form of sand, ceramic sand, or the like. Thus, a particle 10 or many particles 10 need only obstruct the ability of the fissure 84 to close, and may "prop" open the fissures 84 precluding the rock 86 or the pieces of rock 86 from settling back into alignment with one another.

Thus, the particles 10 both alone and in collected piles act as proppants left behind by the fluid flow 82, by virtue of the particles 10b captured. As a practical matter, it is the substrate 12 that acts as a proppant. The polymers 18 may eventually be worn off, or released by a water-soluble binder, but can easily be compressed, distorted, or cut. Regardless, as the fissures 84 open, they are back filled and close in at choke points and settling points collecting the substrate 12.

Continuing to refer to FIG. 6B, while referring generally to FIGS. 1-10, a formation 80 when fractured into individual pieces of stone 86, may form various passages 84 or fissures 84 therein. To the extent that proppant materials 10 lose the adhered particles 18 or powders 18, once hydrated or mixed into the fluid 82, the substrate 12 is then in a position to be deposited by eddies, slower flows, turning corners, and the like. Thus, when the other materials 18 that have acted sails, drifting the substrate 12 with the fluid 82, have been removed, then the substrate 12 can more easily settle out. Accordingly, near corners, in small crevices, in dead corners, and the like, the particles 10, largely stripped of their added constituent powders 18 (in whatever phase at that point) may then drop out of the fluid 82 in a slow flow.

Once two portions of rock 86 separate from one another, forming a passage 84 of some size, a supply of proppant 10b may then prevent that rock portion 86 from moving back into its exact position, necessarily forming passages 84 on virtually every side. Where a single particle 10 of substrate 12 may drop out of the fluid 82 and collect, many more may likewise collect. Accordingly, the various particles 10b illustrated in FIG. 6B may collect, forming substantial support for various edges, corners, and the like of various rock 86. The result is that a small material, in comparatively small quantities, supporting an edge, or a particular region of a rock 86 in the formation 80 may nevertheless maintain a large network of passages 84 as a direct result.

In stone formations having stronger tensile strength, fractures may produce less debris to act as natural proppants. Nevertheless, in addition to the particles 10 constituting primarily substrate material 12 at this point, the passages 84 may be maintained open as is the objective with fracturing.

Figure 7:
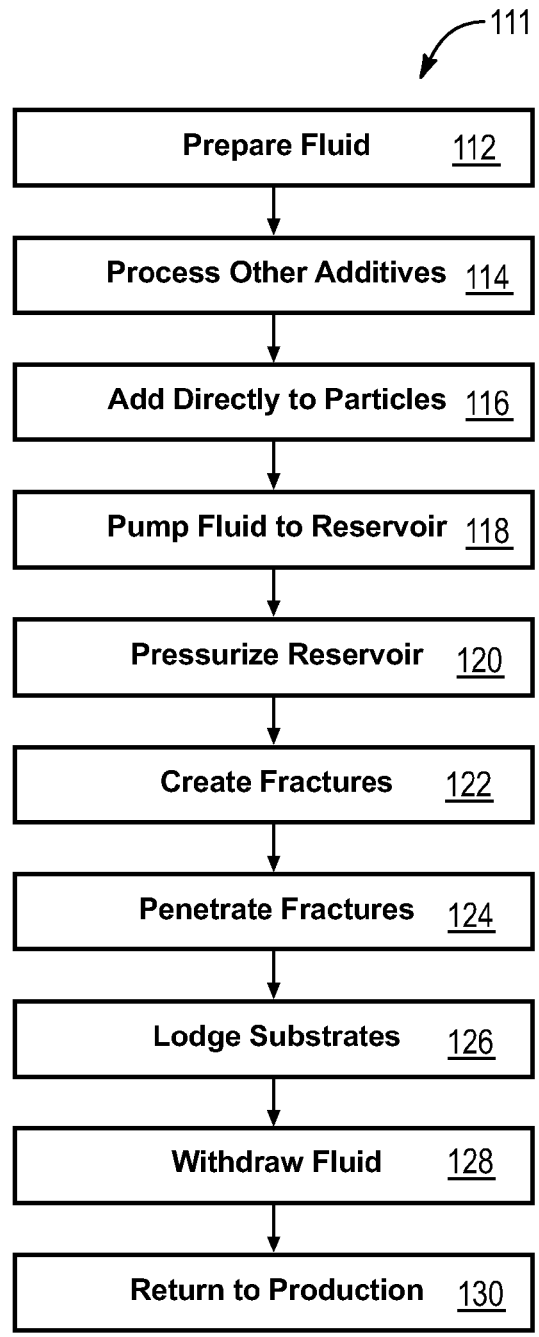
FIG. 7 is a schematic block diagram of a fracturing and propping process using compositions and methods in accordance with the invention

Referring to FIG. 7, a process 111 may include preparing 112 a fluid 82. Processing 114 other additives other than the particles 10 may be done according to any suitable methods, including prior art processes. Adding 116 directly to the fluid 82, the particles 10 as described hereinabove, may be done in such a manner that the operators need not wait for absorption or any other processes to take place. Additional energy for elevating temperature is not required, neither mixing or the like, other than adding 116 directly particles 10 in to the flow 82. The flow 82 will immediately grab the particles 10 according the principles of fluid dynamics in which fluid drag is dependent upon a shape factor of the particle 10, the density of the fluid 82, the square of velocity of the fluid, and so forth, as defined in engineering fluid mechanics.

The fluid 82 now bearing the particles 10 would be immediately pumped 118 into the formation 80 that is the reservoir 80 of an oil field. Eventually, pressurizing 120 the reservoir by pressurizing the fluid 82 results in creating 122 fractures 84 or fissures 84 within the formation 80 by breaking up the rock 86 of the formation 80. A fracture 84 with enough displacement may make a site for material 10 to stagnate and collect.

Creating 122 fracture lines throughout the formation 80 is followed by penetrating 124, by the particles 10 borne in the fluid 82 into the passages 84 or fissures 84 in the rock 86 of the formation 80. Whenever the flow 82 of fluid 82 carries a particle 10 to a choke point 108 in a passage 84, as illustrated in FIG. 6, a particle 10 will be lodged as illustrated in the inset of FIG. 6, a particle 10 with its polymer 18 still secured and intact may be lodged. Similarly, the substrate 12 may be lodged 126 and the polymer 18 may stripped therefrom by the consequent or subsequent flowing of material in the flow 82. Likewise, piles of stagnant particles 10 may backfill spaces, precluding rock 86 settling back in.

After the lodging 126 or propping 126 of the fissures 84 by the substrate 12, in the particles 10, the passages 84 will remain open. These fissures 84 may then be used to later withdraw 128 the fluid 82 from the formation 80. Thereafter, returning 130 the formation 80 to production may occur in any manner suitable. For example, heat may be added to the formation, liquid may be run through the formation as a driver to push petroleum out, or the like.

Figure 8:
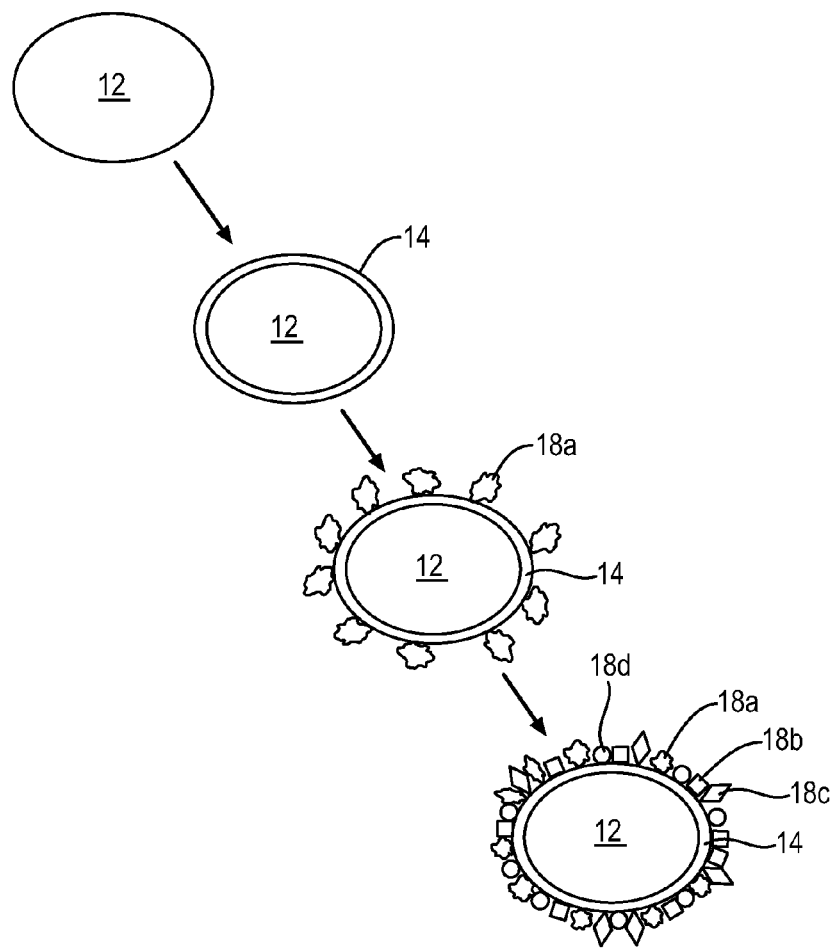
FIG. 8 is a schematic diagram of processes illustrating alternative options for coating, in which particles being adhered to the binder layer may be added sequentially or simultaneously by species or constituent particles.
Figure 9:
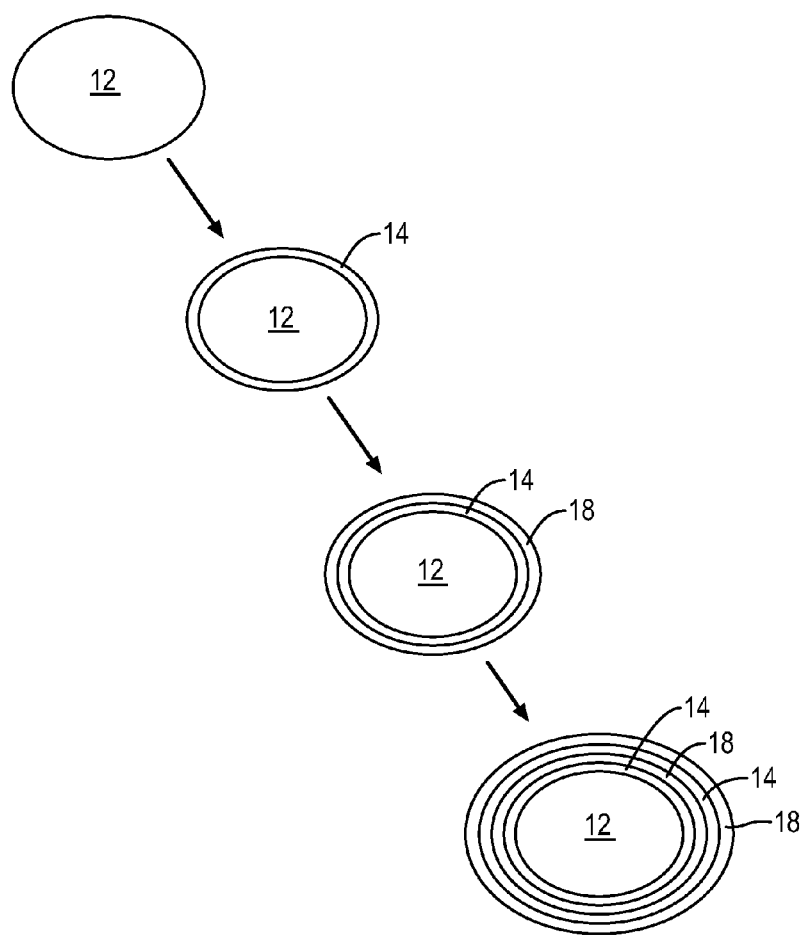
FIG. 9 is a schematic diagram of an alternative coating process in which multiple binding layers are added over previous binding layers and layers of particles.
Figure 10:
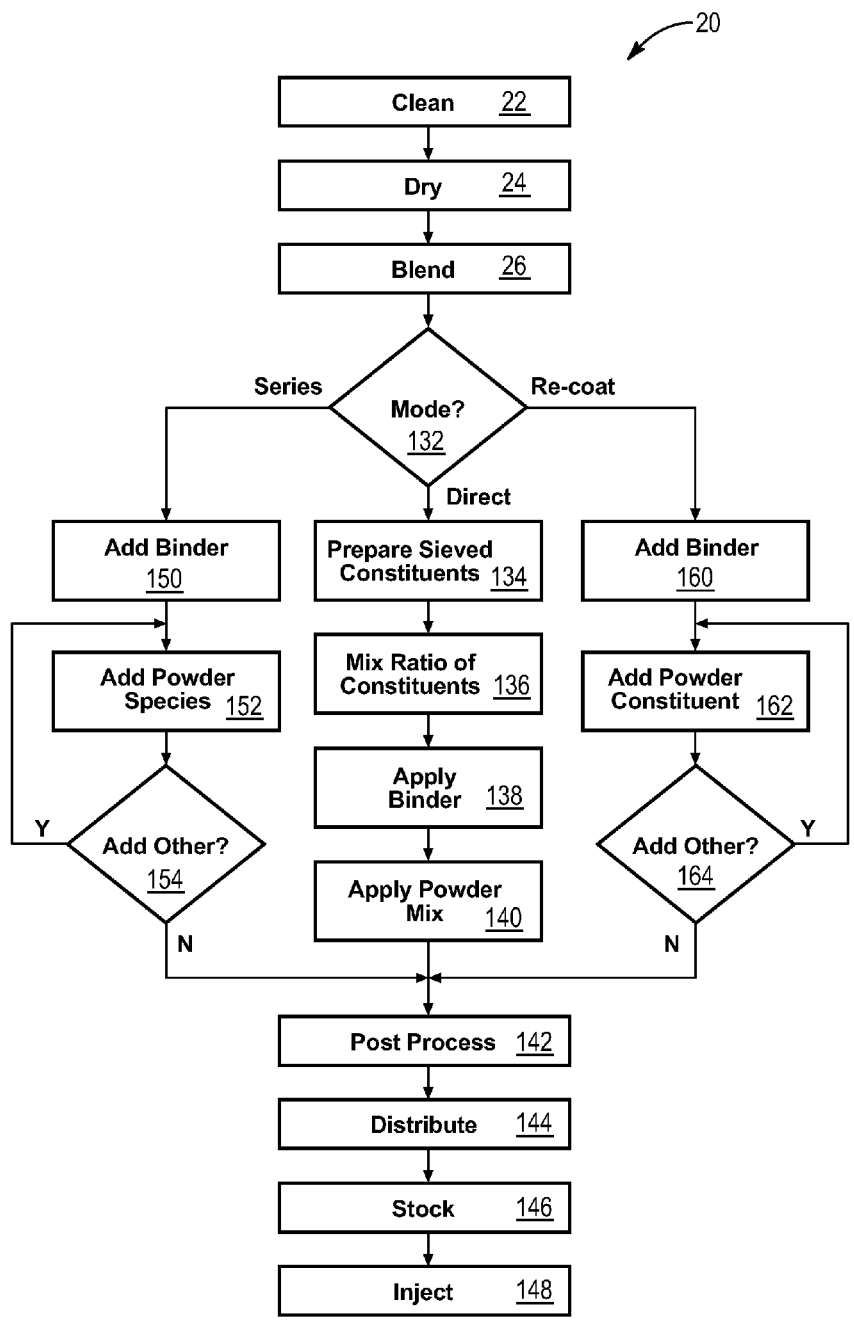
FIG. 10 is a schematic block diagram of some alternative coating processes, including direct coating, sequentially adding particular constituents, and sequentially adding binder and particulate constituents to the particles.

Referring to FIGS. 8-10, while continuing to refer generally to FIGS. 1-10, in various alternative embodiments, multiple constituents may be used as the particles 18 or powder 18 held by the binder 14 to the substrate 12. For example, in various alternative embodiments, one or more other constituents may be added in addition to friction reducers. In the embodiments described hereinabove, the polymeric powders 18 added to the substrate 12 by the tacky or otherwise adhering binder material 14 operated partly as a friction reducer but also as a sill encouraging drifting of the particles 10 with the flow of the fluid 82 or flow 82 in the fracture fluid 82. Thus, hydrophillic powder 18 served multiple purposes.

Meanwhile, as described hereinabove, such polymers may be bonded to the outer surface of the binder 14, thus rendering themselves more susceptible to absorbing water and being stripped of by friction against the walls 88 of various passages 84 in the formation 80. Accordingly, such materials may typically be used in combination with others in various fractures. It has been found effective to include a friction reducing material at a fraction of about 0 to about 10 percent of the total coating granules 18 or powder 18 adhered to the binder 14.

Similarly, biological organisms can change the pH in the water 82 or fluid 82 used for the fracture process. Accordingly, biocides or bacteriacides may eliminate the bacteria or reduce its population in order to avoid changes in the mechanical properties of the fluid 82 as well as changing the pH and thereby the corrosiveness of the fluid 82.

In the contemplated embodiment, such materials such as sodium hypochlorite as a powder or crystal form may be used as one of the constituents for the powder 18 to be bound by the binder 14. Likewise, chlorine dioxide may also be applied by a powder formed of a crystal and form thereof. Other biocides that may be included may be gouteraldehyde as a liquid, or as the constituents thereof in solid form. Similarly, quaternary ammonium chloride may be provided as a solid and therefore as a powder, or as a liquid.

Liquids may be included in the binder 14. Alternatively, the liquid constituents may instead be separated from (or not dissolved in) their solvents in order to provide powders 18 for adhering to the particles 10. Thus, the foregoing liquids as well as tetrakis hydroxhydroxymethyl-phosphonium sulfate may be similarly treated.

As one or even as the only constituent, a particular material may be used as powder 18 adhered to the substrate 12 as part of a particle 10. Any one or more may be combined appropriately. Biocides, typically appear to be suitable in the range of from about 0 to about 3 percent of the particles 18 or powder 18 secured to the substrate 12.

Oxygen scavengers also assist in changing pH as well as preventing corrosion, by removing available oxygen from the fluid 82. Removal of oxygen prevents oxidation, commonly known as rust or corrosion. Thus, the liners, drilling equipment, and other tubular materials may increase their life and reliability and overall integrity of the well by reducing oxygen in the fluid 82. Accordingly, from about 0 to about 3 percent of an oxygen scavenger may be included as part of the coating 18 or the powder 18 adhered to each substrate 12.

Similarly, a clay stabilizer may be included in a proportion of from about 0 to about 3 percent of the coating 18. Thus, clay stabilizers that are used in the fluid 82 may be modified or restricted from swelling or shifting. For example, choline chloride as well as tetramethyl ammonium chloride as well as sodium chloride (salt) may all be provided as powders 18 to be bonded to the substrate 12 by a binder 14.

Likewise, scaling inhibitors may be included at a rate of from about 0 to about 3 percent of the powder 18 adhered to the substrate 12 or of the total weight of the product. Scaling involves the deposition on various conduits and walls, typically in pipes of various minerals, such as carbonates. Changes in pH, changes in temperature, changes in various concentrations of other materials including that of the scaling material may cause scale to accumulate. Accordingly, scale inhibitors may be added as particles 18 in an overall mix, or as part of another coating process.

For example, various copolymers of acrylamides as well as sodium acrylate are scale inhibitors that may be secured to the substrate 12 by the binder 14. Similarly, sodium polycarboxylate and phosphonic acid salt may all be provided in a solid form. All may be comminuted to a powder 18, and sieved to a common size corresponding to that of other materials. Accordingly, mixed in a proper ratio, the powders 18 may actually be compositions of numerous constituents in suitable proportions.

Likewise, a gelling agent may be added in a proportion of from about 0 to about 10 percent as a powder 18 secured to the substrate 12 of particle 10. A function of gelling agents is to alter viscosity. This improves suspension of proppants, such as the substrate 12, sand, or the like, in water. Typically, the speed or velocity with which gravity or other effects may drift a heavy substrate 12 or particle 10 out of solution to leave it elsewhere, is controlled to a large extent by the relative viscosity of the liquid fluid 82 through which the particles 10 are passing. Accordingly, increasing the viscosity tends to keep the particles 10 entrained and more evenly distributed within the fluid 82.

Accordingly, various gelling agents, or a single gelling agent selection may be used as a constituent forming the powder 18 adhered to a substrate 12. Typical processes describe hearinabove and hereinafter illustrate that solid particles may be inducted into the flow 82 or the fluid 82 almost instantly when introduced as the particulates 10. Thus, rather than floating on top during extensive mixing, such materials may be drawn quickly as part of the particles 10 discharged into the fluid 82 at the well head.

Various experiments have shown the utility and ability to add many of these materials. Generally, anything that can be maintained stable for a suitable period of time may be added as powder 18 to a suitable binder 14 holding it to a substrate 12. Thus, various hydrophilic polymers, including polyacrylamides and polyacrylates may be added. Guar gum, various guar derivatives, polysaccharide blends all have the mechanical properties to be suitable as constituents of the powder 18 of particles 10.

Referring to FIG. 8, in one embodiment of a process in accordance with the invention, a substrate 12 may have added to it a layer of binder 14. To the binder 14 may be added a particular powder 18a or additive 18a in solid form to be bound to the substrate 12 by the binder 14. In this particular embodiment, the powder 18a is added first, in a particular fraction. Thereafter, various other constituents may be added in series as the powders 18b, 18c, 18d, illustrated by differing shapes of particles. For example, the particles or powder 18a is illustrated by an irregular shape, the powder 18b by a rectangular shape, 18c by a diamond shape, and 18d by a circular shape. These shapes are merely schematic in order to show the addition of various materials.

Continuing to refer to FIG. 8, the process may also operate by a method of first mixing each of the different powders 18, including up to about 10 or more. Typically, additives in the range of from about 5 to about 9 different constituents may be comminuted and sieved (sorted) in order to maintain all at approximately the same range of sizes.

In this way, by grinding to powder (comminuting) and then sorting with a sieve, the various constituent materials may then be treated mechanically as generic materials, mechanically equivalent. Thus, all may be mixed together.

An important feature here is to avoid disparate sizes, and particularly the inclusions of too many fines. Ultra fine particles tend to provide less included volume in each powder particle, and thus occupy more surface area of the available binder 14 and the surface area of the substrate 12, thus inhibiting even coating and the addition of other constituents. Thus, in such an embodiment, the powder particles 18a, 18b, 18c, 18d, and so forth may all be mixed in the exact proportion desired, usually as a fraction or percentage of the total weight of particles 10, and each may then be included in a mixed supply (e.g., bin, etc.) having the proportions desired, of each and every constituent. Thus, the process described with respect to FIGS. 1 and 2 hereinabove may be used directly, with the powder 18 simply being a mix of other individual constituent chemicals as powders. Thus, all constituents may be added "in parallel," simultaneously.

Referring to FIG. 9, in an alternative embodiment, the substrate 12 may have added to it a binder 14, after which a layer of particles 18 may be added to the binder. Following this, an additional layer of binder 14 may be added to which additional particles 18 may be adhered.

In this embodiment, the additional layers of binder 14 and particles 18 may provide sequential de-layering of the various powders 18 during the process of flowing through the bore and into the formation 80. Nevertheless, it has been found that adhering a supply of particles 18 or powder 18 to a single layer of binder 14, provides adequate surface area, adequate binding, and sufficient area to hold a wide variety of constituent chemicals all adhered in a single coating process.

Referring to FIG. 10, while continuing to refer generally to FIGS. 1-10, one embodiment of a process 20 may be illustrated with the cleaning 22, drying 24, and blending 26 as described hereinabove. Meanwhile, a decision 132 determines the mode of coating. For example, if the decision is to coat directly, then preparing 134 sieved constituents may include comminuting and sorting constituents, each sieved or otherwise sorted in order to provide a consistent size range for each.

Following the preparation 134 of the constituents, mixing 136 is needed for the constituents in the suitable ratios or percentages. This provides a single mixture of powdered particulates 18 suitable for bonding to a substrate 12. Applying 138 a binder is followed by applying 140 the powder 18 to the binder 14 in coating the substrate 12 as described hereinabove.

Following preparation of the of the granular particulates 10, postprocessing may include bagging, may include additional drying, or may include protection against elements to which the material 10 will be exposed.

Post processing 142 may be followed by distribution 144 to various destinations. Distribution 144 may include, or may be followed up by stocking the distributed 144 product 10 at various sites for use. Ultimately, injecting 148 the granular material 10 into the fluid 82 for fracturing may complete the preparation and use of the product 10 in accordance with the invention. Thereafter, the processes described with respect to FIGS. 3-6B occur as a consequence of the configuration of the granular material 10.

In certain alternative embodiments, as illustrated in FIGS. 8 and 9, the mode decision 132 may involve adding powder 18 in series. For example, adding 150 a binder may be followed by adding 152 a powder species. Thereafter, a decision 154 may determine whether to add another species. If the decision is affirmative, then additional species may be added 152 until the coating is completed. Thereafter, when no other additions are to be made, according to the decision step 154, then postprocessing 142 continues, and the process 20 continues to ejection 148.

Similarly, the process of FIG. 9 illustrates the process in which adding 160 a binder 14 is followed by adding 162 a powder constituent, after which a decision 164 results in adding 160 more binder before adding 162 more of a powder constituent. Thus, adding 152 powder only, compared to adding 160 binder 14 and adding 162 additional powdered constituents 18, reflect certain of the embodiments such as FIG. 9. Nevertheless, the embodiment of preparing 134 sieved constituents, through applying 140 the powder 18 as a mixture, is also illustrated in FIG. 8, or represented thereby, as described hereinabove.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method of augmenting a fracturing fluid, the method comprising:
   providing a fluid;
   providing a substrate, constituted as particles, each discrete;
   providing a water soluble material as a binder;
   providing a first composition, containing a polymer, characterized by a chemistry, and formed as a powder;
   coating the particles individually with the binder;
   forming granules by coating the binder on the particles individually with the powder; and
   distributing the first composition in the fluid by introducing the granules into the fluid, wherein the polymer expands an effective diameter of the granules by absorbing the fluid.

2. The method of claim 1, wherein the fluid is moving as a carrier, characterized by a viscosity, and the polymer is selected based on its effectiveness to increase in size by absorbing the fluid.

3. The method of claim 1, wherein the granules are formed off-site, remote from the fluid, and introduced directly into the fluid on-site, proximate the bore.

4. The method of claim 3, wherein the substrate has a first density and the powder has a second density, the first density being greater than the second density.

5. The method of claim 4, wherein the first and second densities are selected, and the size of the granules is selected to effect sinking the polymer, by the substrate, into the fluid.

6. The method of claim 5, wherein an absorption rate and amount of the fluid absorbed by the polymer are selected to be effective to increase drag by the fluid acting on the granules.

7. The method of claim 6, wherein the absorption of the fluid by the polymer is effective to distribute the granules throughout a cross-section of flow of the fluid.

8. The method of claim 7, wherein the first composition comprises a plurality of polymers, distinct from one another.

9. The method of claim 8, wherein each polymer of the plurality of polymers is comminuted to a size range common to the plurality of polymers.

10. The method of claim 9, wherein the plurality of polymers comprises at least two polymers selected from:
    a friction reducer; and
    an oxygen scavenger.

11. The method of claim 10, wherein the substrate is a proppant selected from sand, a ceramic, a rock product, and another manufactured, granular material.

12. The method of claim 11, wherein:
    the friction reducer is selected from acrylamides; and
    the oxygen scavenger includes at least one of an ammonium and a sulfur compound.

13. A method of augmenting a fracturing fluid, the method comprising:
    providing a fluid;

providing a substrate, constituted as particles, each discrete;
providing a binder wherein the binder is water soluble;
providing a first composition, containing a polymer, characterized by a chemistry, and formed as a powder;
coating the particles individually with the binder;
forming granules by coating the binder on the particles individually with the powder, wherein the polymer expands an effective diameter of the granules by absorbing the fluid; and
distributing the first composition in the fluid by introducing the granules into the fluid.

14. A method of augmenting a fracturing fluid, the method comprising:
providing a fluid;
providing a substrate, constituted as particles, each discrete;
providing a binder wherein the binder is water soluble;
providing a first composition, containing a polymer, characterized by a chemistry, and formed as a powder;
coating the particles individually with the binder;
forming granules by coating the binder on the particles individually with the powder, wherein the polymer expands an effective diameter of the granules by absorbing the fluid; and
distributing the first composition in the fluid by introducing the granules into the fluid, wherein the binder is formed of a thickness of coating on the substrate and of a chemistry selected to dissolve during transport of the granules down a bore toward a formation.

* * * * *

UNITED STATES PATENT AND TRADEMARK OFFICE
CERTIFICATE OF CORRECTION

| | | |
|---|---|---|
| PATENT NO. | : 9,057,014 B2 | Page 1 of 1 |
| APPLICATION NO. | : 13/418227 | |
| DATED | : June 16, 2015 | |
| INVENTOR(S) | : Calder Hendrickson et al. | |

It is certified that error appears in the above-identified patent and that said Letters Patent is hereby corrected as shown below:

Title Page, Item (12) delete "Hendrickson" and insert --Hendrickson et al.--.
Title Page, Item (75) Inventor, should read
--(75) Inventors: Calder Hendrickson, Lubbock, TX (US); Tommy K. Thrash, Lubbock, TX (US)--

Signed and Sealed this
Fifth Day of January, 2016

Michelle K. Lee
*Director of the United States Patent and Trademark Office*